United States Patent [19]

Hoehn

[11] 4,013,672

[45] Mar. 22, 1977

[54] 2,5,7,8-TETRAHYDRO-1,2,4,5,6-PENTAAZABENZO[6,7]-CYCLOHEPTA[1,2,3-CD]-AS-INDACENES

[75] Inventor: Hans Hoehn, Tegernheim, Germany

[73] Assignee: E. R. Squibb & Sons, Inc., Princeton, N.J.

[22] Filed: Mar. 15, 1976

[21] Appl. No.: 666,540

[52] U.S. Cl. .................... 260/296 P; 424/263; 260/295 F

[51] Int. Cl.² ........................... C07D 471/14

[58] Field of Search .................. 260/296 P

[56] References Cited

OTHER PUBLICATIONS

*Chemical Abstracts*, Fifth Decennial Index, p. 1655s (1960).
*Chemical Abstracts*, 6th Collective Index, p. 1558s (1964).
*Chemical Abstracts*, 7th Collective Index, p. 2878s (1969).

*Primary Examiner*—John D. Randolph
*Attorney, Agent, or Firm*—Lawrence S. Levinson; Merle J. Smith

[57] ABSTRACT

New derivatives of 2,5,7,8-tetrahydro-1,2,4,5,6-pentaazabenzo[6,7]cyclohepta[1,2,3-cd]-as-indacenes have the general formula

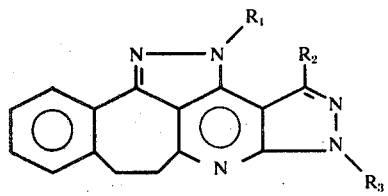

They are useful as psychotropic agents.

10 Claims, No Drawings

2,5,7,8-TETRAHYDRO-1,2,4,5,6-PENTAAZABENZO[6,7]-CYCLOHEPTA[1,2,3-CD]-AS-INDACENES

SUMMARY OF THE INVENTION

This invention relates to new derivatives (and salts) of 2,5,7,8-tetrahydro-1,2,4,5,6-pentaazabenzo[6,7]cyclohepta[1,2,3-cd]-as-indacenes. These new compounds have the general formula

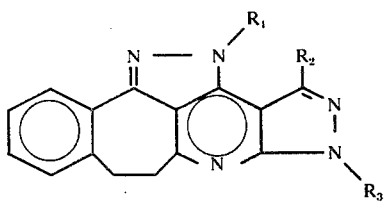

$R_1$ is hydrogen, lower alkyl or hydroxy-lower alkyl. $R_2$ and $R_3$ each is hydrogen, lower alkyl or phenyl.

DETAILED DESCRIPTION

The new compounds of formula I are prepared by the following series of reactions.

A 5-aminopyrazole of the formula

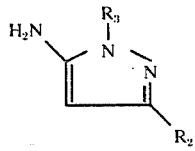

[prepared according to the procedure described in Z.f. chemie 10, 386–388 (1970)] is reacted with a phenylpropionyl malonic acid diethyl ester of the formula

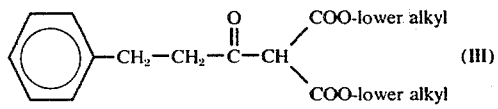

[prepared according to the procedure described in J. Chromatog. 47, 479 (1970)] by heating at a temperature of about 120° C. in the presence of polyphosphoric acid, producing a compound of the formula

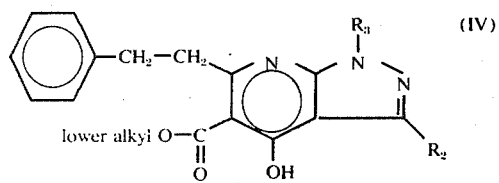

This intermediate of the formula IV is saponified by means of a basic agent like sodium hydroxide, potassium hydroxide, etc. to yield an acid of the formula

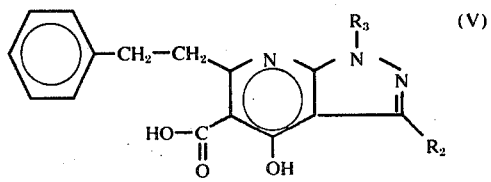

The compound of formula V is then cyclized by heating at a temperature of about 120° C using polyphosphoric acid as the ring closure agent, to produce a compound of the formula

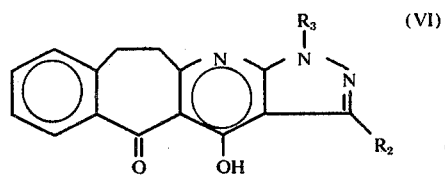

The tetracyclic heterocycle of formula VI is treated with an inorganic acid chloride or bromide such as phosphorus oxychloride, phosphorus oxybromide, thionyl chloride, etc. to yield a compound of the formula

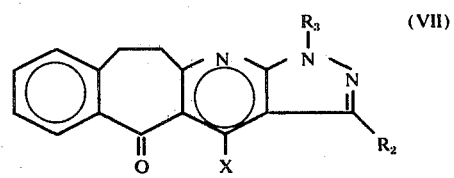

wherein X is Cl or Br.

Treatment of the compound of formula VII with a hydrazine of the formula

at room or elevated temperature produces the product of formula I.

The lower alkyl groups represented by the symbols are straight or branched chain hydrocarbon groups having up to seven carbon atoms, e.g., methyl, ethyl, propyl, isopropyl, butyl, isobutyl, t-butyl, pentyl, hexyl, heptyl, etc. The $C_1$–$C_4$; and especially $C_1$–$C_2$, members are preferred. The hydroxy-lower alkyl groups represented by $R_1$ include a hydroxy group attached to such alkyl groups, preferably on the terminal carbon. The same members are preferred, especially 2-hydroxyethyl.

Preferred are those compounds of formula I wherein $R_1$ is hydrogen, lower alkyl, especially methyl, or hydroxylower alkyl, especially, hydroxyethyl; $R_2$ is hydrogen; and $R_3$ is lower alkyl, especially ethyl. Preferably only one of $R_2$ and $R_3$ is other than hydrogen.

The compounds of formula I form salts which are also part of this invention. The salts include acid-addition salts, particularly the non-toxic, physiologically acceptable members. The bases of formula I form salts by reaction with a variety of inorganic and organic acids providing acid addition salts including, for example, hydrohalides (especially hydrochloride and hydrobromide), sulfate, nitrate, borate, phosphate, oxalate, tartrate, malate, citrate, acetate, ascorbate, succinate, benzene-sulfonate, methanesulfonate, cyclohexanesulfamate and toluenesulfonate. The acid addition salts frequently provide a convenient means for isolating the product, e.g., by forming and precipitating the salt in an appropriate medium in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention are psychotropic agents and can be used as ataractic agents for the relief of anxiety and tension states, for example, in mice, cats, rats, dogs and other mammalian species. For this purpose a compound or mixture of compounds of formula I or physiologically acceptable salt thereof is preferably administered orally, but parenteral routes such as subcutaneously, intramuscularly, intravenously or intraperitoneally in the described dosages, can also be employed. A single dose, or preferably 2 to 4 divided daily doses, provided on a basis of about 1 to 50 mg. per kilogram per day, preferably about 10 to 50 mg. per kilogram per day, is appropriate as indicated in the Rat Conflict Test.

The compounds of the invention can be utilized by formulating in compositions as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

Injectable compositions contain the active compound of formula I in a sterile vehicle such as water for injection or a natural or synthetic vegetable oil such as sesame oil, cottonseed oil, peanut oil, coconut oil or the like or a synthetic vehicle such as ethyl oleate. Antioxidants, preservatives or the like may be included according to accepted pharmaceutical practice.

The following examples are illustrative of the invention and constitute especially preferred embodiments. They also serve as models for the preparation of other members of the group which can be produced by suitable substitution of starting materials. All temperatures are in degrees celsius.

EXAMPLE 1

2,5,7,8-Tetrahydro-5-ethyl-1,2,4,5,6-pentaazabenzo[6,7]-cyclohepta[1,2,3-cd]-as-indacene a. 1-Ethyl-4-hydroxy-6-(2-phenylethyl)-1H-pyrazolo[3,4-b]pyridine-5-carboxylic acid, ethyl ester 43.6 g. of (3-phenylpropionyl)malonic acid, diethyl ester (0.15 mol.) are added to a stirred mixture of 16.5 g. of 5-amino-1-ethylpyrazole (0.15 mol.) and 220 g. polyphosphoric acid. The mixture is heated to 120° (bath temp.) for 50 minutes. After the mixture has cooled to room temperature, 250 ml. of water are added in portions and stirring is continued for 20 minutes. Then the aqueous phosphoric acid solution is decanted and the undissolved residue is treated with 200 ml. of water and aqueous ammonia (10%) to neutralize the mixture. The mixture is extracted with chloroform, washed twice with water, dried with sodium sulfate and evaporated to yield 39 g. of oily product. The oil is dissolved in about 250 ml. of ether and ethereal hydrochloric acid added to yield 35 g. (62%) of 1-ethyl-4-hydroxy-6-(2-phenylethyl)-1H-pyrazolo[3,4-b]pyridine-5-carboxylic acid, ethyl ester, hydrochloride; m.p. 153°–155° (ethanol/ethyl acetate 1:1).

b. 1-Ethyl-4-hydroxy-6-(2-phenylethyl)-1H-pyrazolo[3,4-b]pyridine-5-carboxylic acid 64 g. of 1-ethyl-4-hydroxy-6-(2-phenylethyl)-1H-pyrazolo[3,4-b]pyridine-5-carboxylic acid, ethyl ester, hydrochoride (0.17 mol.), dissolved in 800 ml. of aqueous sodium hydroxide (20%), are heated at 80°–85° (bath temp.) for 44 hours. The solution with the saponified ester is treated with charcoal, filtered and then acidified with half-concentrated hydrochloric acid. The precipitated 1-ethyl-4-hydroxy-6-(2-phenylethyl)-1H-pyrazolo[3,4-b]pyridine-5-carboxylic acid is filtered off, washed with water and dried in a desiccator to give 46.5 g. (88%) of 1-ethyl-4-hydroxy-6-(2-phenylethyl)-1H-pyrazolo[3,4-b]pyridine-5-carboxylic acid, m.p. 160°–161° (abs. ethanol).

c. 1-Ethyl-10,11-dihydro-4-hydroxybenzo[4,5]cyclohepta[1,2-b]pyrazolo[4,3-e]pyridin-5(1H)one 46.6 g. of 1-ethyl-4-hydroxy-6-(2-phenylethyl)1H-pyrazolo[3,4-b]pyridine-5-carboxylic acid (0.15 mol.) and 300 g. of polyphosphoric acid are heated at 200°–220° (bath temp.) with stirring for 20 minutes. After the mixture has cooled to room temperature, 700 ml. of ice water are added continuously and stirring is continued until the compound becomes crystalline. The collected ketone is then dissolved in chloroform and the solution is washed with water, treated with charcoal and dried with sodium sulfate. Evaporation of the solution yields 30.3 g. (69%) of 1-ethyl-10,11-dihydro-4-hydroxybenzo[4,5]cyclohepta[1,2-b]pyrazolo[4,3-e]pyridin-5(1H)one, m.p. 154°–156° (hexane).

Dissolving the compound in ether and adding ethereal hydrochloric acid provides the hydrochloride salt, m.p. 166° (dec.).

d. 4-Chloro-1-ethyl-10,11-dihydrobenzo[4,5]cyclohepta[1,2-b]pyrazolo[4,3-e]pyridin-5(1H)one 26.5 g. of 1-ethyl-10,11-dihydro-4-hydroxybenzo[4,5]cyclohepta[1,2-b]pyrazolo[4,3-e]pyridin-5(1H)one (0.09 mol.) are refluxed in 350 ml. of phosphorus oxychloride for 5 hours. The excess phosphorus oxychloride is removed in vacuo and the residue is treated with water and extracted with ether. The ethereal solution is washed twice with water, dried (sodium sulfate) and then evaporated to give 26 g. (93%) of 4-chloro-1-ethyl-10,11-dihydrobenzo[4,5]cyclohepta[1,2-b]pyrazolo[4,3-e]pyridin-5(1H)one, m.p. 111°–113° (hexane/cyclohexane 2:1).

e. 2,5,7,8-Tetrahydro-5-ethyl-1,2,4,5,6-pentaazabenzo[6,7]cyclohepta[1,2,3-cd]-as-indacene A mixture of 11.0 g. of 4-chloro-1-ethyl-10,11-dihydrobenzo[4,5]cyclohepta[1,2-b]pyrazolo[4,3-e]pyridin5(1H)one (0.035 mol.), 4.5 g. of hydrazine hydrate 98% (0.09 mol.) and 125 ml. of abs. ethanol is refluxed for 3 hours with stirring. Then the reaction solution is filtered while hot and allowed to crystallize in a refrigerator. The crystallized 2,5,7,8-tetrahydro-5-ethyl-1,2,4,5,6-pentaazabenzo[6,7]cyclohepta[1,2,3-cd]as-indacene which is filtered off, washed with alcohol and ether, melts at 229°–231°. Evaporation of the mother liquor to dryness and treatment with water yields a further crop of 1.9 g. of the product. Total yield 97%. Recrystallization from ethanol elevates the melting point to 230°–232°.

EXAMPLE 2

5-Ethyl-2,5,7,8-tetrahydro-2-methyl-1,2,4,5,6-pentaazabenzo[6,7]cyclohepta[1,2,3-cd]-as-indacene 8.4 g. of 4-chloro-1-ethyl-10,11-dihydrobenzo[4,5-]cyclohepta[1,2-b]pyrazolo[4,3-e]pyridin-5(1H)one (0.027 mol.) are dissolved in 100 ml. of absolute ethanol by heating. To the stirred hot solution there are added 3.0 g. of methylhydrazine (0.065 mol.) and the mixture is stirred at 70° for 20 minutes. After this time, the solution is filtered while hot and allowed to crystallize, yielding 6.4 g. (79%) of 5-ethyl-2,5,7,8-tetrahydro-2-methyl-1,2,4,5,6-pentaazabenzo[6,7]cyclohepta[1,2,3-cd]-as-indacene. The product, washed with alcohol and ether, melts at 140°–141°. A sample recrystallized from cyclohexane melts at 140°–142°.

EXAMPLE 3

5-Ethyl-7,8-dihydro-1,2,4,5-pentaazabenzo[6,7]cyclohepta[1,2,3-cd]-as-indacene-2(5H)-ethanol To a hot solution of 9.3 g. of 4-chloro-1-ethyl-10,11-dihydrobenzo[4,5]cyclohepta[1,2,-b]pyrazolo[4,3-e]pyridin5(1H)one (0.03 mol.) in 150 ml. absolute ethanol are added 5.5 g. of 2-hydroxyethylhydrazine (0.072 mol.) and the solution is kept at reflux temperature for 5 minutes. The reaction mixture is allowed to stand overnight, the crystallized 5-ethyl-7,8-dihydro-1,2,4,5-pentaazabenzo[6,7]cyclohepta[1,2,3-cd]-as-indacene-2(5H)-ethanol is filtered off and washed with absolute ethanol and ether, yield 7.0 g. (70%), m.p. 202°–204° (ethanol).

EXAMPLE 4

5-Ethyl-2,5,7,8-tetrahydro-2-ethyl-1,2,4,5,6-pentaazabenzo[6,7]cyclohepta[1,2,3-cd]-as-indacene By substituting ethylhydrazine for the methylhydrazine in the procedure of Example 2, 5-ethyl-2,5,7,8-tetrahydro-2-ethyl-1,2,4,5,6-pentaazabenzo[6,7]cyclohepta[1,2,3-cd]-asindacene is obtained.

EXAMPLE 5

5-Ethyl-2,5,7,8-tetrahydro-2-butyl-1,2,4,5,6-pentaazabenzo[6,7]cyclohepta[1,2,3-cd]-as-indacene By substituting butylhydrazine for the methylhydrazine in the procedure of Example 2, 5-ethyl-2,5,7,8-tetrahydro-2-butyl-1,2,4,5,6-pentaazabenzo[6,7]cyclohepta[1,2,3-cd]-as-indacene is obtained.

EXAMPLE 6

5-Ethyl-7,8-dihydro-1,2,4,5,6-pentaazabenzo[6,7]cyclohepta[1,2,3-cd]-as-indacene-2(5H)-butanol By substituting (4-hydroxybutyl)hydrazine for the 2-hydroxyethylhydrazine in the procedure of Example 3, 5-ethyl-7,8-dihydro-1,2,4,5,6-pentaazabenzo[6,7-]cyclohepta[1,2,3-cd]-as-indacene-2(5H)-butanol is obtained.

EXAMPLE 7

2,5,7,8-Tetrahydro-1,2,4,5,6-pentaazabenzo[6,7]cyclohepta[1,2,3-cd]-as-indacene

By substituting the 4-chloro-10,11-dihydrobenzo[4,5]cyclohepta[1,2-b]pyrazolo[4,3-e]pyridin-5(1H)-one (obtained in Example 6) for the 4-chloro-1-ethyl-10,11-dihydrobenzo[4,5]cyclohepta[1,2-b]pyrazolo[4,3-e]pyridin5(1H)-one in the procedure of Example 2 and also substituting hydrazine for the methylhydrazine, 2,5,7,8-tetrahydro-1,2,4,5,6-pentaazabenzo[6,7]-cyclohepta[1,2,3-cd]-as-indacene is obtained EXAMPLE 8

2,5,7,8-Tetrahydro-5-phenyl-1,2,4,5,6-pentaaza benzo[6,7]cyclohepta[1,2,3-cd]-as-indacene By substituting 5-amino-1-phenylpyrazole for the 5-amino-1-ethylpyrazole in part a of Example 1 and continuing as in that Example, 2,5,7,8-tetrahydro-5-phenyl-1,2,4,5,6-pentaazabenzo[6,7]cyclohepta[1,2,3-cd]as-indacene is obtained.

EXAMPLE 9

2-Ethyl-2,5,7,8-tetrahydro-3-phenyl-1,2,4,5,6-pentaazabenzo[6,7]cyclohepta[1,2,3-cd]-as-indacene By substituting 5-amino-3-phenylpyrazole for the 5-amino-1-ethylpyrazole in part a of Example 1 and continuing as in that Example but substituting ethylhydrazine for the hydrazine hydrate in part e, 2-ethyl-2,5,7,8-tetrahydro-3-phenyl-1,2,4,5,6-pentaazabenzo[6,7]cyclohepta[1,2,3-cd]-as-indacene is obtained.

EXAMPLE 10

2,5,7,8-Tetrahydro-3,5-diethyl-1,2,4,5,6-pentaazabenzo[6,7]cyclohepta[1,2,3-cd]-as-indacene By substituting 5-amino-1,3-diethylpyrazole for the 5-amino-1-ethylpyrazole in part a of Example 1 and continuing as in that Example, 2,5,7,8-tetrahydro-3,5-diethyl-1,2,4,5,6-pentaazabenzo[6,7]cyclohepta[1,2,3-cd]-as-indacene is obtained.

EXAMPLE 11

5-Ethyl-2,5,7,8-tetrahydro-2-methyl-1,2,4,5,6-pentaazabenzo[6,7]cyclohepta[1,2,3-cd]-as-indacene, hydrochloride Addition of ethereal hydrochloric acid to a solution of 5-ethyl-2,5,7,8-tetrahydro-2-methyl-1,2,4,5,6-pentaazabenzo[6,7]cyclohepta[1,2,3-cd]-as-indacene in ethyl acetate provides the hydrochloride, yield 92%, m.p. 208°–211° (dec.).

EXAMPLE 12

5-Ethyl-7,8-dihydro-1,2,4,5,6-pentaazabenzo[6,7-]cyclohepta[1,2,3-cd]-as-indacene-2(5H)-ethanol, hydrochloride Ethereal hydrochloric acid added to a solution of 5-ethyl-7,8-dihydro-1,2,4,5,6-pentaazabenzo[6,7]cyclohepta[1,2,3-cd]-as-indacene-2(5H)-ethanol in ethylacetate gives raise to the formation of the hydrochloric acid salt, yield 89%; m.p. 219°–221° (dec.).

What is claimed is:

1. A compound of the formula

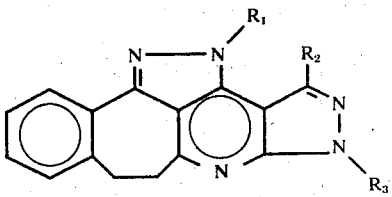

wherein
$R_1$ is hydrogen, lower alkyl or hydroxy-lower alkyl;
$R_2$ and $R_3$ each is hydrogen, lower alkyl or phenyl;
and acid addition salts thereof.
2. A compound as in claim 1 wherein $R_2$ is hydrogen.
3. A compound as in claim 1 wherein $R_3$ is lower alkyl.
4. A compound as in claim 1 wherein $R_1$ is hydrogen.
5. A compound as in claim 1 wherein $R_1$ is lower alkyl.
6. A compound as in claim 1 wherein $R_1$ is hydroxy-lower alkyl.
7. A compound as in claim 1 wherein $R_1$ is hydrogen, lower alkyl or hydroxy-lower alkyl; $R_2$ is hydrogen; and $R_3$ is lower alkyl.
8. A compound as in claim 2 wherein $R_1$ is hydrogen and $R_3$ is ethyl.
9. A compound as in claim 2 wherein $R_1$ is methyl and $R_3$ is ethyl.
10. A compound as in claim 2 wherein $R_1$ is 2-hydroxy-ethyl and $R_3$ is ethyl.

* * * * *